United States Patent [19]

Martin

[11] 4,327,216

[45] Apr. 27, 1982

[54] PROCESS FOR PRODUCING 2,3,5,6-TETRACHLOROPYRIDINE AND 3,5,6-TRICHLOROPYRIDIN-2-OL

[75] Inventor: Pierre Martin, Rheinfelden, Switzerland

[73] Assignee: Ciba-Geigy Corporation, Ardsley, N.Y.

[21] Appl. No.: 209,783

[22] Filed: Nov. 24, 1980

[30] Foreign Application Priority Data

Nov. 30, 1979 [CH] Switzerland ............... 10660/79

[51] Int. Cl.$^3$ ............................................. C07D 213/61
[52] U.S. Cl. ................................. 546/250; 546/303; 546/345
[58] Field of Search ................. 546/250, 303, 345

[56] References Cited

U.S. PATENT DOCUMENTS

| | | | |
|---|---|---|---|
| 3,244,586 | 4/1966 | Rigterink | 260/959 X |
| 3,355,278 | 11/1967 | Weil | 71/113 X |
| 3,420,833 | 1/1969 | Taplin | 546/345 X |
| 3,538,100 | 11/1970 | Smith | 546/345 |
| 3,694,322 | 9/1972 | Ikeda | 203/79 X |
| 3,694,332 | 9/1972 | Parker | 546/345 X |
| 3,694,332 | 9/1972 | Parker | 204/73 R |
| 3,751,421 | 8/1973 | Nyquist et al. | 546/302 |
| 3,993,654 | 11/1976 | Dean et al. | 546/345 |
| 4,133,675 | 1/1979 | Schurter et al. | 71/78 X |
| 4,245,098 | 1/1981 | Steiner et al. | 546/250 |

FOREIGN PATENT DOCUMENTS

| | | | |
|---|---|---|---|
| 1445683 | 1/1969 | Fed. Rep. of Germany | 546/345 |
| 2141632 | 4/1972 | Fed. Rep. of Germany | . |
| 991526 | 5/1965 | United Kingdom | . |
| 1024399 | 3/1966 | United Kingdom | . |
| 1050378 | 12/1966 | United Kingdom | 546/345 |
| 1334922 | 10/1973 | United Kingdom | . |

OTHER PUBLICATIONS

Rigterink, et al., J. Agr. Food Chem., 14, (1966), pp. 304–306.
Hertog, et al., Receuil Trav. Chim., 70, (1951), pp. 182–190.

*Primary Examiner*—Joseph Paul Brust
*Attorney, Agent, or Firm*—Frederick H. Rabin

[57] ABSTRACT

2,3,5,6-Tetrachloropyridine and/or 3,5,6-trichloropyridin-2-ol can be obtained, using a simple novel process, by reacting trichloroacetyl chloride, in the presence of a catalyst, for example copper (I) chloride or -bromide, with acrylonitrile. 2,3,5,6-Tetrachloropyridine and 3,5,6-trichloropyridin-2-ol are suitable for producing various active substances, particularly for producing insecticides, herbicides and fungicides.

8 Claims, No Drawings

PROCESS FOR PRODUCING 2,3,5,6-TETRACHLOROPYRIDINE AND 3,5,6-TRICHLOROPYRIDIN-2-OL

The present invention relates to a novel process for producing 2,3,5,6-tetrachloropyridine and 3,5,6-trichloropyridin-2-ol.

The processes hitherto known for producing 2,3,5,6-tetrachloropyridine and 3,5,6-trichloropyridin-2-ol are in various respects unsatisfactory. 2,3,5,6-Tetrachloropyridine can be obtained by high-temperature chlorination of pyridine or pyridine derivatives, such as 3,5-dichloro-2-trichloromethylpyridine and 2,6-dichloropyridine (about 200°–600° C., preferably about 350°–600° C.); by reaction of glutaric acid dinitrile with chlorine in the gaseous phase at elevated temperatures (about 400°–600° C.); or by chlorination of ε-caprolactam or cyclohexanone-oxime at elevated temperatures. There are formed however in these processes, besides the desired symmetrical tetrachloropyridine, a series of other highly chlorinated pyridines, which have to be separated (cp. for example the British Patent Specification Nos. 1,050,378, 1,334,922 and 991,526, the U.S. Pat. Nos. 3,420,833 and 3,538,100, and also the German Offenlegungsschriften Nos. 1,445,683 and 2,141,632). 2,3,5,6-Tetrachloropyridine and 3,5,6-trichloropyridin-2-ol can be obtained also by stepwise chlorination of 6-bromo- or 6-chloro-2-ethoxypyridine [cp. Recueil trav. chim. 70, 182 (1951)].

A further possibility is to proceed with the high-temperature chlorination with excess chlorinating agent more or less selectively as far as pentachloropyridine, and to subsequently reduce the chlorine atom in the 4-position either with zinc (cp. for example U.S. Pat. No. 3,993,654) or electrolytically (cp. U.S. Pat. No. 3,694,332). In the case of reduction with zinc, there occur large amounts of zinc salts, a factor which is undesirable from an ecological standpoint. High-temperature chlorination, electrolytic reduction as well as the (electrolytic) generation of zinc necessitate on the other hand a high consumption of energy. The pentachloropyridine itself has moreover a relatively severe skin- and eye-irritating effect. 3,5,6-Trichloropyridin-2-ol can be produced by hydrolysis of 2,3,5,6-trichloropyridine (for example Recueil trav. chim. 70, 182 (1951)).

From the British Patent Specification No. 1,024,399 is also known that halogen compounds, such as sulfonyl halides, allyl halides and halogenonitriles, can be added by reaction, in the presence of catalysts, to ethylenically unsaturated compounds, such as olefins with conjugated double bonds, acrylic acid and acrylic acid derivatives. Exclusively open-chain products are obtained by the process.

A novel process has now been found by which 2,3,5,6-tetrachloropyridine and 3,5,6-trichloropyridin-2-ol can be produced with avoidance of the above disadvantages, in a simple, economical and ecologically favourable manner, with use of cheap, readily accessible starting products.

The process according to the invention comprises reacting trichloroacetyl chloride, in the presence of a catalyst, with acrylonitrile to obtain 2,3,5,6-tetrachloropyridine and/or 3,5,6-trichloropyridin-2-ol.

It is surprising that by using the selected starting materials according to the invention, with displacement of the chlorine atoms, 2,3,5,6-tetrachloropyridine or 3,5,6-trichloropyridin-2-ol is obtained directly, that is to say, that, with use of a starting product (trichloroacetyl chloride) in which three chlorine atoms are bound to the same C atom, there are obtained final products in which the three chlorine atoms are located on different C atoms and in the desired positions (in the 3-, 5- and 6-position). By virtue of this unexpected reaction, the costly and involved high-temperature chlorination operation can be dispensed with.

As catalysts for the addition reaction of trichloroacetyl chloride with acrylonitrile, it is possible to use in the process according to the invention compounds known per se, such as metals of the main group VIII and of the subgroups VIa, VIIa, Ib and IIb of the periodic system (according to Lehrbuch der anorgan. Chemie [Textbook of inorganic Chemistry], Hollemann-Wiberg, W. de Gruyter & Co., Berlin), for example iron, cobalt, nickel, ruthenium, rhodium, palladium, chromium, molybdenum, manganese, copper and zinc. These metals can be in the elementary form or in the form of compounds. Suitable compounds of this type are for example oxides, halides, sulfates, sulfites, sulfides, nitrates, acetates, stearates, citrates, carbonates, cyanides and rhodanides, as well as complexes with ligands, such as phosphines, phosphites, benzoyl- and acetylacetonates, nitriles, isonitriles and carbon monoxide.

Examples which may be mentioned are: copper(II) oxide, iron(III) oxide; Cu(I)-, Cu(II)-, Fe(II)- and Fe(III)-bromides and -iodides and particularly -chlorides, zinc chloride, as well as the chlorides of ruthenium, of rhodium, of palladium, of cobalt and of nickel; Cu(II)-sulfate, Fe(II)- and Fe(III)-sulfate, Cu(II) nitrate and iron(III) nitrate; manganese(III) acetate, copper(II)-acetate, copper(II) stearate, iron(III) citrate, Cu(I)-cyanide; ruthenium(II) dichloro-tris-triphenylphosphine, rhodium-dichloro-tris-triphenylphosphine; chromium- and nickel-acetylacetonate, copper(II) acetylacetonate, iron(III) acetylacetonate, cobalt(II)- and cobalt(III)-acetylacetonate, manganese(II) acetylacetonate, copper(II)-benzoylacetonate; iron carbonyl-cyclopentadienyl complex; molybdenum carbonylcyclopentadienyl complex, chromium-tricarbonylaryl complexes, ruthenium(II) acetate complex, chromium- and molybdenum-hexacarbonyl, nickel tetracarbonyl, iron pentacarbonyl and cobalt- and manganese-carbonyl.

It is also possible to use mixtures of the stated metals with metal compounds and/or other additives, such as copper powder in combination with one of the aforementioned copper compounds; mixtures of copper powder with lithium halides, such as lithium chloride, or with isocyanides, such as tert-butylisocyanide; mixtures of iron powder with iron(III) chloride, optionally with the addition of carbon monoxide; mixtures of iron(III) chloride and benzoin; mixtures of iron(II)- and iron(III)-chloride and trialkylphosphites; and mixtures of iron pentacarbonyl and iodine.

Preferred catalysts are iron(II)- and iron(III)-salts and -complexes, particularly iron(II)- and iron(III)-chloride, as well as iron powder; ruthenium(III) chloride, ruthenium(II) dichloro-tris-triphenylphosphine, copper powder, copper bronze, copper(I)- and copper(II)-salts and -complexes, such as Cu(I) chloride, Cu(II) chloride, Cu(I) bromide, Cu(II) bromide; Cu(II) acetate, Cu(II)-acetylacetonate, Cu(II) benzoylacetonate, Cu(II) sulfate, Cu(II) nitrate, Cu(I) cyanide and Cu(I) iodide.

Particularly preferred catalysts are copper powder, copper bronze, copper(I)- and copper(II)-chloride or -bromide and copper(I) iodide, as well as mixtures thereof.

The catalysts are used generally in amounts of about 0.01 to 10 mol %, preferably 0.1 to 5 mol %, relative to the acrylonitrile.

The reaction of trichloroacetyl chloride with acrylonitrile is advantageously performed in the presence of an organic solvent. Suitable organic solvents are those in which the catalysts are sufficiently soluble, or which can form complexes with the catalysts, which however are inert to the trichloroacetyl chloride and acrylonitrile. Examples of solvents of this kind are alkyl nitriles, particularly those having 2–5 C atoms, such as acetonitrile, propionitrile and butyronitrile; 3-alkoxypropionitriles having 1 to 2 C atoms in the alkoxy moiety, such as 3-methoxypropionitrile and 3-ethoxypropionitrile; aromatic nitriles, especially benzonitrile; also acrylonitrile (that is to say, excess reagent as solvent); aliphatic ketones preferably having all together 3–8 C atoms, such as acetone, diethyl ketone, methylisopropyl ketone, diisopropyl ketone, methyl-tert-butyl ketone; alkyl and alkoxyalkyl esters of aliphatic monocarboxylic acids having all together 2–6 C atoms, such as formic acid-methyl and -ethyl esters, acetic acid-methyl, -ethyl, -n-butyl and -isobutyl esters, as well as 1-acetoxy-2-methoxyethane; cyclic ethers, such as tetrahydrofuran, tetrahydropyrane and dioxane; N,N-dialkylamides of aliphatic monocarboxylic acids having 1–3 C atoms in the acid moiety, such as N,N-dimethylformamide, N,N-dimethylacetamide, N,N-diethylacetamide and N,N-dimethylmethoxyacetamide; ethylene glycol- and diethylene-glycol dialkyl ethers having 1–4 C atoms in each of the alkyl moieties, such as ethylene glycol dimethyl, -diethyl and -di-n-butyl ethers; diethylene glycol diethyl and -di-n-butyl ethers; and hexamethylphosphoric acid triamide (hexametapol).

Particularly preferred solvents are alkyl nitriles having 2–5 C atoms, and 3-alkoxypropionitriles having 1 or 2 C atoms in the alkoxy moiety, particularly acetonitrile, butyronitrile and 3-methoxypropionitrile. Also excess acrylonitrile (that is to say, excess reagent as solvent) is another particularly preferred solvent.

The reaction to give 2,3,5,6-tetrachloropyridine and/or 3,5,6-trichloropyridin-2-ol is preferably performed between about 70° and 220° C., especially between 130° and 200° C. The reaction can be carried out either in an open or closed vessel. It is performed particularly preferably in a closed system at a pressure corresponding to the respective reaction temperature, which pressure can be for example within the range of 0 to 50 bars.

Mixtures of 2,3,5,6-tetrachloropyridine and 3,5,6-trichloropyridin-2-ol are generally formed in the process according to the invention. The reaction can however be selectively controlled by variation of the reaction conditions. 2,3,5,6-Tetrachloropyridine can also be subsequently hydrolysed, by methods known per se, to 3,5,6-trichloropyridin-2-ol, which in its turn can be readily converted into 2,3,5,6-tetrachloropyridine [cp. for example Recueil, 70, 182 and 187 (1951)].

Elevated temperatures (above about 140° C.) and operation in a closed system, optionally with the addition of HCl-forming agents, such as phosgene, aluminium trichloride, trialkylammonium chlorides, $POCl_3$ and $PCl_5$, are particularly preferred conditions for a selective reaction favouring the formation of 2,3,5,6-tetrachloropyridine. Alternatively, the reaction mixture can also be subsequently treated with HCl or with agents splitting off HCl, such as phosgene, $POCl_3$, $PCl_5$ or $CH_3P(O)Cl_2$. Aftertreatment of the reaction mixture with agents supplying hydoxyl ions, such as mixtures of water and NaOH, $NaHCO_3$, $Na_2CO_3$ or tertiary amines, such as triethylamine, tributylamine, pyridine, and so forth, yields exclusively 3,5,6-trichloropyridin-2-ol.

Also 3,4,5,6-tetrachloro-3,4-dihydropyridone-(2) can be formed as an intermediate in the reaction according to the invention.

2,3,5,6-Tetrachloropyridine and 3,5,6-trichloropyridin-2-ol can be isolated in a customary manner and optionally purified, for example by crystallisation, distillation, sublimation, chromatography and especially by steam distillation.

2,3,5,6-Tetrachloropyridine and 3,5,6-trichloropyridin-2-ol are known compounds, and are suitable for producing various active substances, particularly for producing insecticides, herbicides and fungicides [cp. for example U.S. Pat. Nos. 4,133,675, 3,244,586, 3,355,278 and 3,751,421; French Patent Specification No. 2,171,939 and also J. Agr. Food Chem. 14, 304 (1966)].

EXAMPLE 1

181.8 g of trichloroacetyl chloride, 53.1 g of acrylonitrile, 4 g of copper(I) chloride and 400 ml of acetonitrile are held for 2 hours at 180° C. in a 1 liter enamel autoclave. The reaction mixture is subsequently concentrated by evaporation, and the residue is extracted with hot n-pentane. The concentrated crystalline extract is digested with methanol, and the occurring crystals (2,3,5,6-tetrachloropyridine; m.p. 90°–91° C.) are filtered off. The methanolic solution is concentrated by evaporation, and the residue is crystallised from n-hexane to thus obtain 3,5,6-trichloropyridin-2-ol, m.p. 170°–171° C.

EXAMPLE 2

The procedure is carried out as in Example 1 except that after separation of 2,3,5,6-tetrachloropyridine, distillation with superheated steam is performed to yield 3,5,6-trichloropyridin-2-ol in the form of snow-white crystals; m.p. 168°–170° C. $^1$H-NMR spectrum (DMSO-$d_6$/$D_2O$) in ppm: 8.07 (s).

EXAMPLE 3

When the reaction described in Example 1 is performed at 115° C. and repeatedly interrupted in order to take samples, the 3,3,5,6-tetrachloro-3,4-dihydropyridone-(2) of the formula

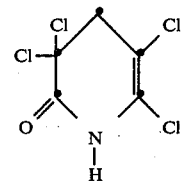

can be identified as an intermediate and isolated; m.p. 127°–128° C. 3,3,5,6-Tetrachloro-3,4-dihydropyridone-(2) precipitates on cooling and disappears again in the further course of the reaction. IR Spectrum ($CHCl_3$) in $cm^{-1}$: 1720 (CO), 1665 (C=C). $^1$H-NMR Spectrum ($CDCl_3$/$D_2O$) in ppm: 3.57 (s).

EXAMPLE 4

The reaction mixture described in Example 1 is kept at 140° C. for 8 hours. The reaction mixture, concentrated by evaporation, is subjected directly to steam distillation to thus obtain white crystals which consist, according to spectroscopic data (IR and $^1$H-NMR spectrum), of a mixture of 2,3,5,6-tetrachloropyridine and 3,5,6-trichloropyridin-2-ol.

EXAMPLE 5

Example 4 is repeated with the difference that the crude reaction mixture, concentrated by evaporation, is taken up in ethanol, and 10% sodium hydroxide solution is then added until the solution remains alkaline. The ethanol is evaporated off and steam distillation is subsequently carried out to thus obtain pure 3,5,6-trichloropyridin-2-ol; m.p. 170°–172° C.

EXAMPLE 6

Example 4 is repeated with the exception that the same amount by weight of $CH_3P(O)Cl_2$ is added to the concentrated reaction mixture, and the reaction mixture is maintained at 180° C. (bath temperature) for 2½ hours. After cooling, it is carefully decomposed with ice water, and then distilled with steam to yield exclusively 2,3,5,6-tetrachloropyridine; m.p. 90° C.

EXAMPLE 7

The reaction mixture obtained according to Example 4 is passed through a tube at 180° C. with a slight HCl counterflow. The pyrrolisate obtained is distilled with steam to obtain 2,3,5,6-tetrachloropyridine (m.p. 89°–91° C.) in the form of white flakes.

What is claimed is:

1. A process for the production of a mixture of 2,3,5,6-tetrachloropyridine and 3,5,6-trichloropyridin-2-ol which comprising reacting trichloroacetic acid chloride with acrylonitrile, in an organic solvent inert to trichloroacetic acid chloride and acrylonitrile, in the presence of a catalyst selected from the group consisting of metals and metal compounds of the main group VIII or the subgroups Ib, IIb, VIa or VIIa of the periodic system, at a temperature of between about 70° and 220° C. in a closed system and at a pressure corresponding to the respective reaction temperature.

2. The process according to claim 1 comprising the further step of treating the reaction mixture with HCl or with an agent splitting off HCl, thereby producing 2,3,5,6-tetrachloropyridine as the sole end product.

3. A process according to claim 1 comprising the further step of treating the reaction mixture with an agent supplying hydroxyl ions, thereby producing 3,5,6-trichloropyridin-2-ol as the sole end product.

4. A process according to claim 1, wherein the catalyst used is selected from the group consisting of iron(II) chloride, iron(III) chloride, iron powder, ruthenium(III) chloride, ruthenium(II) dichloro-tris-triphenylphosphine, copper powder, copper bronze, copper(I) chloride, copper(II) chloride, copper(I) bromide, copper(II) bromide, copper(I) iodide, copper(II) acetate, copper(II) acetylacetonate, copper(II) benzoylacetonate, copper(II) sulfate, copper(II) nitrate and copper(I) cyanide.

5. A process according to claim 1, wherein the catalyst used is selected from the group consisting of copper powder, copper bronze, copper(I) chloride, copper(II) chloride, copper(I) bromide, copper(II) bromide or copper(I) iodide, and a mixture thereof.

6. A process according to claim 1, wherein the reaction is performed at a temperature of between 130°–200° C.

7. A process according to claim 1, wherein the organic solvent used is an alkyl nitrile having 2–5 carbon atoms or a 3-alkoxypropionitrile having 1 or 2 carbon atoms in the alkoxy moiety.

8. A process according to claim 1, wherein the organic solvent used is selected from the group consisting of acetonitrile, butyronitrile, 3-methoxypropionitrile and acrylonitrile.

* * * * *